United States Patent [19]

Goga

[11] Patent Number: 5,574,089
[45] Date of Patent: Nov. 12, 1996

[54] WATER-BASED LATEX COMPOSITIONS CONTAINING BORIC ACID

[76] Inventor: John M. Goga, 15 Wildflower Dr., Newark, Del. 19711

[21] Appl. No.: 512,174

[22] Filed: Aug. 7, 1995

[51] Int. Cl.$^6$ .............................. C08L 31/04; A01N 25/04
[52] U.S. Cl. ........................ 524/556; 424/405; 574/553; 574/772.4; 574/772.6; 524/557; 524/570; 524/571; 524/577; 524/579; 528/934; 528/935
[58] Field of Search ..................................... 524/556, 557, 524/570, 571, 577, 579; 574/553, 772.4, 772.6; 528/934, 935; 424/405

[56] References Cited

U.S. PATENT DOCUMENTS

| | | | |
|---|---|---|---|
| 4,079,028 | 3/1978 | Emmons et al. | 524/507 |
| 4,155,892 | 5/1979 | Emmons et al. | 524/507 |
| 5,254,161 | 10/1993 | DeVido et al. | 106/170 |
| 5,290,693 | 3/1994 | Chen et al. | 435/182 |

*Primary Examiner*—Shelley A. Dodson
*Attorney, Agent, or Firm*—Harness, Dickey & Pierce P.L.C.

[57] ABSTRACT

Improved water-based latex compositions are provided comprising a water-based latex emulsion and boric acid. It has been surprisingly found that by adding boric acid to water-based latex emulsions known in the art, micro-organism growth is eliminated. In a preferred composition, the boric acid is present in an amount of about 0.10% to about 10% by weight of the total composition.

17 Claims, No Drawings

WATER-BASED LATEX COMPOSITIONS CONTAINING BORIC ACID

FIELD OF THE INVENTION

The present invention relates generally to water-based latex compositions and more particularly, to water-based latex compositions comprising boric acid to eliminate micro-organism growth.

BACKGROUND OF THE INVENTION

Water-based latex compositions often contain biocides and preservatives to eliminate the growth of micro-organisms present in the compositions. It is important to control micro-organism growth in water-based latex compositions because micro-organisms readily contaminate the latex formulation thus reducing the physical properties of the latex formulation.

Currently, several types of additives are employed to combat micro-organism growth in water-based latex formulations. For example, formaldehyde releasing agents and hydrogen peroxide are regularly added to the latex formulations. Unfortunately, these commonly-used biocide/preservatives are known toxins/carcinogens which require a totally self-contained system during the addition to the final product. Further, the currently-employed preservatives have a limited active shelf life.

It would thus be desirable to provide water-based latex compositions which contain a non-toxic biocide/preservative. It would further be desirable to provide water-based latex compositions which include a non-toxic biocide/preservative and do not require a controlled storage environment or a self-contained system for combining the latex formulation and the biocide/preservative.

SUMMARY OF THE INVENTION

Improved water-based latex compositions are provided comprising a water-based latex emulsion with the addition of boric acid. It has been surprisingly found that by adding boric acid to water-based latex emulsions known in the art, micro-organism growth is eliminated. In a preferred composition, the boric acid is present in an amount of about 0.10% to about 10% and more preferably in an amount of about 0.5 to about 2%, by weight of the total composition.

Additional objects, advantages, and features of the present invention will become apparent from the following description and appended claims.

DETAILED DESCRIPTION OF PREFERRED EMBODIMENTS

Water-based latex compositions comprising water-based latex emulsions and boric acid are provided. It has been unexpectedly found that the addition of boric acid to a water-based latex emulsion eliminates the growth of micro-organisms present in the composition. Thus, boric acid acts as a non-toxic biocide/preservative in the water-based latex compositions of the present invention.

In a preferred composition, boric acid is added to a water-based latex emulsion such as vinyl acrylic (vinyl acetate/butyl acrylate (reductive/oxidation catalyst system)), vinyl acrylic (thermal catalyst system)), vinyl acetate homopolyer, all acrylic and styrene acrylic, in a range of about 0.10% to about 10%, by weight of the total composition. In a highly preferred embodiment, the water-based latex emulsion has a pH of less than 6.0 and the boric acid is present in an amount of about 0.5% to about 1.0%, by weight of the total composition.

The addition of boric acid to the water-based latex emulsions causes very little pH shift compared to currently-employed preservatives such as formaldehyde. In addition, boric acid serves to stabilize any residual catalyst in the latex that may still have activity. Moreover, the boric acid acts as a thermal stabilizer for non-surfactant all-acrylic and styrene acrylic water-based latex emulsions. Furthermore, the addition of boric acid may act as a viscosity stabilizer for vinyl acetate homo-polymer latex emulsions. Test results indicate that boric acid contains an indefinite active shelf life and the micro-organism eliminating quality remains active in both a thermal and ambient environment.

It will be appreciated that the addition of boric acid as a biocide/preservative as described herein may be applied in a variety of end use applications including but not limited to, interior/exterior house paints, industrial caulks and sealants, and industrial coatings and mastics. Furthermore, the addition of boric acid will provide increased bacteria and fungus resistance and protection in commercial products currently available in the market. The following specific examples will further describe the present invention.

SPECIFIC EXAMPLE 1

Boric acid can be added to the latex in a powder or aqueous form. Boric acid is soluble in water, thus it will readily disperse into the latex formulation. Subsequent to adding the boric acid, an agitating system is used to distribute the boric acid uniformly throughout the latex formulation. Boric acid may also be added at the beginning of the manufacturing process or during the polymerization reaction when acting as a thermal stabilizer. Alternatively, boric acid can be added at the completion of the polymerization reaction when acting as a residual catalyst stabilizer or a preservative/biocide reagent.

SPECIFIC EXAMPLE 2

Four samples of different water-based latex emulsions were tested to determine their biocidal-efficacy against *Escherichia Coli* (*E. Coli*, a bacteria), *Pseudomonas Aeruginosa* (*Ps. Aeruginosa*, a bacteria), *Aspergillus Niger* (*A. Niger*, a fungus), and *Candida Albicans* (*C. Albicans*, a yeast). The samples contained 0.5% and 1.0% boric acid, by weight of the total composition. In addition, a control containing the commercially available biocide/preservative at 0.20 to 0.25%, by weight of the total composition. The samples included vinyl acrylic (reduction/oxidation catalyst system), vinyl acrylic (thermal catalyst system), all acrylic, and styrene acrylic.

The tests were conducted by preparing the samples described above with a standardized initial inoculum level of organisms. All samples were then tested after one, three and seven day periods, and the quantity of organisms present was measured in each sample in cfu per gram.

| | Micro Organism Levels |
| --- | --- |
| ORGANISM | INITIAL INOCULUM LEVELS (cfu/gm) |
| *Ps. Aeruginosa* | $4.0 \times 10^7$ |
| *E. Coli* | $1.2 \times 10^7$ |
| *C. Albicans* | $4.3 \times 10^6$ |
| *A. Niger* | $9.0 \times 10^7$ |

Control Sample For Latex (Styrene Acrylic) Treated
With Commercially Available Preservative

| ORGANISM | DAY 1 (cfu/gm) | DAY 3 (cfu/gm) | DAY 7 (cfu/gm) |
|---|---|---|---|
| Ps. Aeruginosa | $1.5 \times 10^4$ | *$2.0 \times 10^4$ | $11.3 \times 10^5$ |
| E. Coli | $2.4 \times 10^4$ | *$1.3 \times 10^4$ | $15.4 \times 10^4$ |
| C. Albicans | $2.2 \times 10^4$ | *$1.9 \times 10^4$ | $17.4 \times 10^4$ |
| A. Niger | $8.8 \times 10^3$ | *$4.8 \times 10^3$ | $15.6 \times 10^4$ |

Styrene Acrylic Treated With 0.5% Boric Acid

| ORGANISM | DAY 1 (cfu/gm) | DAY 3 (cfu/gm) | DAY 7 (cfu/gm) |
|---|---|---|---|
| Ps. Aeruginosa | <10 | <10 | <10 |
| E. Coli | <10 | <10 | <10 |
| C. Albicans | <10 | <10 | <10 |
| A. Niger | <10 | <10 | <10 |

Styrene Acrylic Treated With 1.0% Boric Acid

| ORGANISM | DAY 1 (cfu/gm) | DAY 3 (cfu/gm) | DAY 7 (cfu/gm) |
|---|---|---|---|
| Ps. Aeruginosa | <10 | <10 | <10 |
| E. Coli | <10 | <10 | <10 |
| C. Albicans | <10 | <10 | <10 |
| A. Niger | <10 | <10 | <10 |

Control Sample For Latex (All Acrylic) Treated
With Commercially Available Preservative

| ORGANISM | DAY 1 (cfu/gm) | DAY 3 (cfu/gm) | DAY 7 (cfu/gm) |
|---|---|---|---|
| Ps. Aeruginosa | <10 | <10 | <10 |
| E. Coli | <10 | <10 | <10 |
| C. Albicans | <10 | <10 | <10 |
| A. Niger | <10 | <10 | <10 |

All Acrylic Treated With 0.5% Boric Acid

| ORGANISM | DAY 1 (cfu/gm) | DAY 3 (CtLi/gm) | DAY 7 (cfu/gm) |
|---|---|---|---|
| Ps. Aeruginosa | <10 | <10 | <10 |
| E. Coli | <10 | <10 | <10 |
| C. Albicans | <10 | <10 | <10 |
| A. Niger | <10 | <10 | <10 |

All Acrylic Treated With 1.0% Boric Acid

| ORGANISM | DAY 1 (cfu/gm) | DAY 3 (cfu/gm) | DAY 7 (cfu/gm) |
|---|---|---|---|
| Ps. Aeruginosa | <10 | <10 | <10 |
| E. Coli | <10 | <10 | <10 |
| C. Albicans | <10 | <10 | <10 |
| A. Niger | <10 | <10 | <10 |

Control Sample For Latex
(Vinyl Acrylic - Thermal Catalyst) Treated
With Commercially Available Preservative

| ORGANISM | DAY 1 (cfu/gm) | DAY 3 (cfu/gm) | DAY 7 (cfu/gm) |
|---|---|---|---|
| Ps. Aeruginosa | <10 | <10 | <10 |
| E. Coli | <10 | <10 | <10 |
| C. Albicans | <10 | <10 | <10 |
| A. Niger | <10 | <10 | <10 |

Vinyl Acrylic (Thermal Catalyst)
Treated With 0.5% Boric Acid

| ORGANISM | DAY 1 (cfu/gm) | DAY 3 (cfu/gm) | DAY 7 (cfu/gm) |
|---|---|---|---|
| Ps. Aeruginosa | <10 | <10 | <10 |
| E. Coli | <10 | <10 | <10 |
| C. Albicans | <10 | <10 | <10 |
| A. Niger | <10 | <10 | <10 |

Vinyl Acrylic (Thermal Catalyst)
Treated With 1.0% Boric Acid

| ORGANISM | DAY 1 (cfu/gm) | DAY 3 (cfu/gm) | DAY 7 (cfu/gm) |
|---|---|---|---|
| Ps. Aeruginosa | <10 | <10 | <10 |
| E. Coli | <10 | <10 | <10 |
| C. Albicans | <10 | <10 | <10 |
| A. Niger | <10 | <10 | <10 |

Control Sample For Latex
(Vinyl Acrylic - Redox Catalyst) Treated
With Commercially Available Preservative

| ORGANISM | DAY 1 (cfu/gm) | DAY 3 (cfu/gm) | DAY 7 (cfu/gm) |
|---|---|---|---|
| Ps. Aeruginosa | <10 | <10 | <10 |
| E. Coli | <10 | <10 | <10 |
| C. Albicans | <10 | <10 | <10 |
| A. Niger | <10 | <10 | <10 |

Vinyl Acrylic (Redox Catalyst)
Treated With 0.5% Boric Acid

| ORGANISM | DAY 1 (cfu/gm) | DAY 3 (cfu/gm) | DAY 7 (cfu/gm) |
|---|---|---|---|
| Ps. Aeruginosa | <10 | <10 | <10 |
| E. Coli | <10 | <10 | <10 |
| C. Albicans | <10 | <10 | <10 |
| A. Niger | <10 | <10 | <10 |

Vinyl Acrylic (Redox Catalyst)
Treated With 1.0% Boric Acid

| ORGANISM | DAY 1 (cfu/gm) | DAY 3 (cfu/gm) | DAY 7 (cfu/gm) |
|---|---|---|---|
| Ps. Aeruginosa | <10 | <10 | <10 |
| E. Coli | <10 | <10 | <10 |
| C. Albicans | <10 | <10 | <10 |
| A. Niger | <10 | <10 | <10 |

*unidentified contaminating yeast count

The test results indicated that all samples using boric acid to eliminate micro-organism growth contained less than 10 cfu per gram at the end of the one, three and seven day periods.

Those skilled in the art can now appreciate from the foregoing description that the broad teachings of the present invention can be implemented in a variety of forms. Therefore, while this invention has been described in connection with particular examples thereof, the true scope of the invention should not be so limited since other modifications will become apparent to the skilled practitioner upon a study of the specification and following claims.

We claim:

1. A water-based latex composition comprising:
   a) a water-based latex emulsion; and
   b) boric acid.
2. The composition of claim 1, wherein the boric acid is present in an amount of from about 0.10% to about 10% by weight of the total composition.
3. The composition of claim 1, wherein the water-based latex emulsion is a vinyl acrylic.
4. The composition of claim 1, wherein the water-based latex emulsion is a vinyl acetate homopolymer.

5. The composition of claim 1, wherein the water-based latex emulsion is an all acrylic.

6. The composition of claim 1, wherein the water-based latex emulsion is a styrene acrylic.

7. The composition of claim 1, wherein the water-based latex emulsion has a pH of about 6.0 or less.

8. The composition of claim 2, wherein the boric acid is present in an amount of about 0.5% to about 1.0% by weight of the total composition.

9. A method of preparing a water-based latex composition, comprising the steps of
   a. adding boric acid to a water-based latex emulsion, and
   b. agitating the boric acid and the latex emulsion.

10. The method of claim 9, wherein the boric acid is added in an amount of from about 0.10% to about 10% by weight of the total composition.

11. The method of claim 9, wherein the water-based latex emulsion is a vinyl acrylic.

12. The method of claim 9, wherein the water-based latex emulsion is a vinyl acetate homopolymer.

13. The method of claim 9, wherein the water-based latex emulsion is an all acrylic.

14. The method of claim 9, wherein the water-based latex emulsion is a styrene acrylic.

15. The method of claim 9, wherein the water-based latex emulsion has a pH of about 6.0 or less.

16. The method of claim 10, wherein the boric acid is added in an amount of about 0.5% to about 1.0% by weight of the total composition.

17. A method of preparing a water-based latex composition, comprising the steps of
   a. adding boric acid to water, and
   b. forming in the water, in the presence of the boric acid, a water-based latex emulsion by polymerization reaction.

* * * * *

UNITED STATES PATENT AND TRADEMARK OFFICE
CERTIFICATE OF CORRECTION

PATENT NO. : 5,574,089
DATED : November 12, 1996
INVENTOR(S) : John M. Goga and Lawrence S. Heller It is certified that error appears in the above-indentified patent and that said Letters Patent is hereby corrected as shown below:

On the title page, item [19], "Goga" should be --Goga et al.--

On the Title Page under Inventor, insert --Lawrence S. Heller, 2103 North Oaks Boulevard, North Brunswick, NJ 08902--.

Column 1, line 64, "homopolyer" should be --homopolymer--.

Column 3, line 8, "11.3 x 105" should be --*1.3x10$^5$--.

Column 3, line 9, "15.4" should be --*5.4--.

Column 3, line 10, "17.4" should be --*7.4--.

Column 3, line 11, "15.6" should be --*5.6--.

Column 3, line 40, "(CtLi/gm)" should be --(cfu/gm)--.

Signed and Sealed this

Sixth Day of May, 1997

*Attest:*

BRUCE LEHMAN

*Attesting Officer*    Commissioner of Patents and Trademarks